United States Patent
Goode et al.

(10) Patent No.: US 6,936,023 B2
(45) Date of Patent: *Aug. 30, 2005

(54) COMPOSITE VENTILATION TUBE

(75) Inventors: Richard L. Goode, Los Altos, CA (US); F. Barry Bays, Clearwater, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/682,253

(22) Filed: Oct. 10, 2003

(65) Prior Publication Data

US 2004/0077989 A1 Apr. 22, 2004

Related U.S. Application Data

(63) Continuation of application No. 10/028,776, filed on Dec. 28, 2001, now Pat. No. 6,692,455, which is a continuation of application No. 08/427,909, filed on Apr. 26, 1995, now Pat. No. 6,406,453.

(51) Int. Cl.$^7$ .......................... A61M 5/00; A61M 31/00; A61M 35/16; A61F 11/00
(52) U.S. Cl. ........................... 604/8; 604/264; 604/284; 606/109
(58) Field of Search ............................. 604/8–10, 264, 604/284, 534, 523, 271, 275, 514, 104–107, 530, 532–3, 535–36, 540–41; 606/108, 109; 623/11.11

(56) References Cited

U.S. PATENT DOCUMENTS

| | | |
|---|---|---|
| 3,788,327 A | 1/1974 | Donowitz et al. |
| 3,835,863 A | 9/1974 | Goldberg et al. |
| 3,871,380 A | 3/1975 | Heros |
| 3,948,827 A | 4/1976 | Noshiro et al. |
| 4,037,604 A | 7/1977 | Newkirk |
| 4,402,681 A | 9/1983 | Haas et al. |
| 4,568,337 A | 2/1986 | Treharne, III et al. |
| 4,613,640 A | 9/1986 | Deisler et al. |
| 4,695,275 A | 9/1987 | Bruce et al. |
| 4,744,792 A | 5/1988 | Sander et al. |
| 4,886,488 A | 12/1989 | White |
| 4,964,850 A | 10/1990 | Bouton et al. |
| 5,026,378 A | 6/1991 | Goldsmith, III |
| 5,080,650 A | 1/1992 | Hirsch et al. |
| 5,116,327 A | 5/1992 | Seder et al. |
| 5,163,924 A | 11/1992 | Beverly |
| 5,178,623 A | 1/1993 | Cinberg et al. |
| 5,186,168 A | 2/1993 | Spofford et al. |
| 5,246,455 A * | 9/1993 | Shikani ................ 623/10 |
| 5,300,020 A | 4/1994 | L'Esperance, Jr. |
| 5,399,164 A | 3/1995 | Smoke et al. |
| 5,775,336 A * | 7/1998 | Morris ................ 128/857 |
| 5,851,199 A | 12/1998 | Peerless et al. |
| 6,010,463 A | 1/2000 | Lauks et al. |
| 6,027,532 A | 2/2000 | Hobelka |
| 6,146,364 A | 11/2000 | Kawano |
| 6,264,870 B1 | 7/2001 | Håkansson |
| 6,406,453 B1 * | 6/2002 | Goode et al. ............ 604/8 |
| 6,692,455 B2 * | 2/2004 | Goode et al. ............ 604/8 |

* cited by examiner

*Primary Examiner*—Patricia Bianco

(57) ABSTRACT

A medical ventilation tube for placement in an opening formed in an anatomical structure, such as the tympanic membrane of the ear, includes a hollow tubular shaft made of a first material having a hardness or durometer to maintain a passage through the shaft when the medical ventilation tube is placed in the opening, and a flange made of a second material having a hardness or durometer less than that of the first material to permit the flange to deform in response to contact with the anatomical structure during removal of the medical ventilation tube from the opening.

5 Claims, 5 Drawing Sheets

COMPOSITE VENTILATION TUBE

CROSS-REFERENCE TO RELATED PATENT APPLICATIONS

This application is a continuation of U.S. patent application Ser. No. 10/028,776 filed Dec. 28, 2001 and now U.S. Pat. No. 6,692,455 B2, which is a continuation of U.S. patent application Ser. No. 08/427,909 filed Apr. 26, 1995 and now U.S. Pat. No. 6,406,453 B1, the entire disclosures of which are incorporated herein by reference.

BACKGROUND OF THE INVENTION

1. Field of the Invention

The present invention relates generally to medical ventilation tubes and, more particularly, to myringotomy ventilation tubes that can be placed in the tympanic membrane of the ear to drain fluid and alleviate a buildup or reduction of pressure in the middle ear.

2. Description of Prior Art

The installation of tubes in the tympanic membrane, which separates the middle ear from the outer ear, is a well-known remedy for treating inflammation of the middle ear or otitis media. Typically, a myringotomy is performed to create an opening in the tympanic membrane and a vent or drain in the form of a tube is inserted into the opening to permit drainage of fluid from the middle ear to alleviate a buildup, or reduction of pressure in the middle ear cavity. The tube functions to maintain the opening in the tympanic membrane for a sufficient period of time following the surgery to allow pressure to equalize between the middle and outer ears. Frequently, the condition of buildup or reduction of pressure in the middle ear cavity which the tube is intended to alleviate requires that the tube remain in place for a significant period of time ranging in duration from about six to about twenty four months.

A variety of ventilation tubes for insertion into an opening in the tympanic membrane have been introduced over the years. Prior art ventilation tubes without flanges at either end are easy to insert into the myringotomy opening but are disadvantageous in that they can be accidentally extracted from the tympanic membrane. On the other hand, ventilation tubes having flanges at one or both ends are less likely to be accidentally extracted from the tympanic membrane but are difficult to insert into and extract from the myringotomy openings, tending to enlarge the myringotomy openings such that the tendency of the tubes to fall out of the membrane increases. Attempts to fabricate prior art ventilation tubes of softer materials help alleviate problems associated with insertion and removal of the tubes through openings in the tympanic membrane but contribute to problems related to bending or buckling of the tubes during insertion while detracting from the ability of the tube to maintain an opening in the tympanic membrane.

SUMMARY OF THE INVENTION

Accordingly, it is a primary object of the present invention to overcome the disadvantages of the prior art and to improve ventilation tubes of the type used in maintaining an opening in anatomical structures such as the tympanic membrane.

It is another, more specific, object of the present invention to ease insertion of a ventilation tube into an opening in an anatomical structure while preventing inadvertent extrusion and facilitating removal.

Yet another object of the present invention is to prevent enlargement of an opening in an anatomical structure, such as the tympanic membrane, in response to insertion or removal of a medical ventilation tube through the opening.

Still another object of the present invention is to form a ventilation tube as a composite structure made of two or more materials of different durometer.

It is a further object of the present invention to maintain an opening in an anatomical structure by use of a ventilation tube having a hollow shaft made of a rigid or hard material and a flange formed at a distal end of the shaft made of a softer, more flexible material.

The present invention is generally characterized in a medical ventilation tube for placement in an anatomical structure including a hollow tubular shaft having a passage formed therethrough, the hollow tubular shaft being made of a first material having a rigidity to resist bending and maintain the passage in an open condition when the ventilation tube is placed in the anatomical structure, and a flange extending outwardly from the hollow tubular shaft, the flange being made of a second material having a rigidity less than that of the first material to permit the flange to deform in response to contact with the anatomical structure. The first material is preferably a polymer having a durometer no greater than about 100 on the Shore A hardness scale, and the second material is also preferably a polymer having a durometer less than that of the first material but greater than about 20 on the Shore A hardness scale. In a most preferred embodiment, the first material is a polymer having a durometer of about 90 to about 95 on the Shore A hardness scale and a second material is a polymer having a durometer of about 50 on the Shore A hardness scale.

Another aspect of the present invention is generally characterized in a method of making a medical ventilation tube including the steps of forming a hollow tubular shaft from a first material having a rigidity to resist bending and to maintain a passage through the shaft when the ventilation tube is placed in an anatomical structure, and molding a flange onto the hollow tubular shaft using a second material having a rigidity less than that of the first material to permit the flange to be deformed in response to contact with the anatomical structure.

Some of the advantages of the present invention are that the ventilation tube can be inserted into an opening in an anatomical structure, such as the tympanic membrane, without buckling or bending of the hollow shaft, that extrusion of the ventilation tube is prevented while maintaining a passage of substantially constant diameter through the opening, and that the ventilation tube can be formed using a wide range of materials having a variety of properties suitable for improving ease of insertion and removal, preventing extrusion and maintaining structural rigidity of the ventilation tube.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
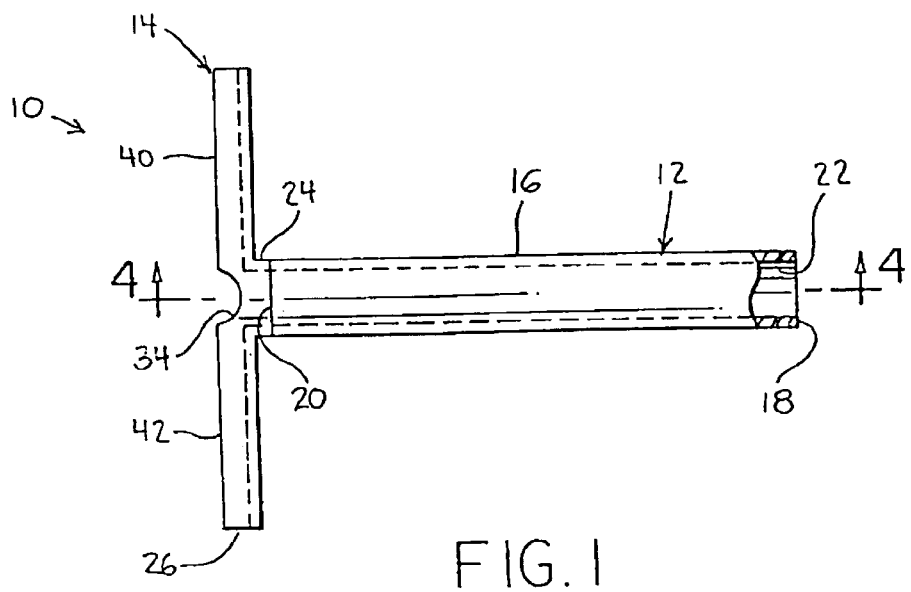
FIG. 1 is a top plan view, partly in section, showing a ventilation tube according to the present invention.

The medical ventilation tube of the present invention can be used to maintain an opening in any anatomical structure within the body; and, accordingly, while the ventilation tube is described herein as a myringotomy ventilation tube for placement in an opening formed in the tympanic membrane of the ear, it will be appreciated that the medical ventilation tube of the present invention can be placed in other naturally occurring and surgically created openings throughout the body.

A ventilation tube 10 according to the present invention, as shown in FIGS. 1–4, includes a hollow tubular body or shaft 12 and a flanged end portion 14. Shaft 12 is formed of a right circular cylinder 16 with a proximal end 18, a distal end 20 and a lumen 22 extending between the proximal and distal ends to define at least part of a passage through an anatomical structure such as the tympanic membrane of the ear. Shaft 12 is preferably made of a medically acceptable plastic or metal material having a hardness or durometer suitable for withstanding axial insertion forces without buckling or bending and for maintaining the passage in a substantially unobstructed, open condition to permit drainage and ventilation of the middle ear over extended periods of time.

Figure 2:
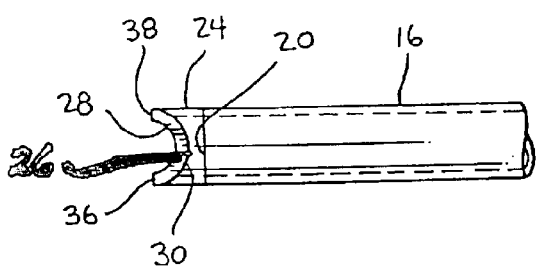
FIG. 2 is a fragmentary side view of the ventilation tube of FIG. 1.
Figure 3:
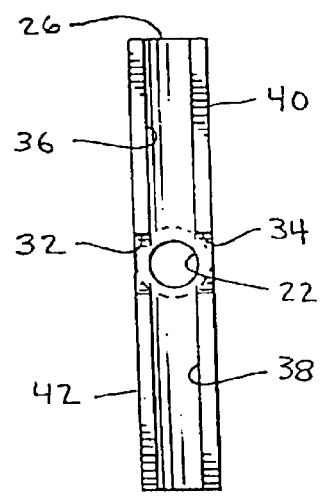
FIG. 3 is a front elevational view of the ventilation tube of FIG. 1.
Figure 4:
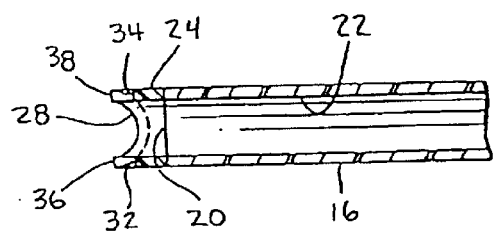
FIG. 4 is a fragmentary side view, in section, taken through line 4—4 in FIG. 1.

End portion 14 includes a cylindrical section 24 extending from the distal end of shaft 12 to a transverse cross-member or flange 26. As best seen in FIG. 2, flange 26 is generally semi-cylindrical in cross-section with a concave side 28 facing distally and a convex side 30 facing proximally to form an abutment surface for contacting the tympanic membrane of the ear around the myringotomy opening. A pair of semi-circular cut-outs or notches 32 and 34 are formed along distal edges 36 and 38 of the flange in opposed relation near the center of the flange to permit bending of the flange from the transverse position shown in FIG. 1 to a collapsed position facilitating removal of the ventilation tube from the tympanic membrane without enlargement of the myringotomy opening. In the collapsed position, opposed ends or ears 40 and 42 of the flange are pivoted about notches 32 and 34 into mating contact along a longitudinal axis of the ventilation tube where they cooperate to form a tubular extension similar in diameter to shaft 12. Cylindrical section 24 and flange 26 are preferably formed as an integral one-piece construction using a medically acceptable metal or plastic material having a hardness or durometer less than that of the shaft to facilitate bending of the flange during insertion and removal of the ventilation tube so as to minimize trauma to the tympanic membrane.

In a preferred embodiment, shaft 12 and flanged end portion 14 are formed of a polymeric material known as C-Flex™ thermoplastic elastomer. The basic formula of the C-Flex™ material is described in U.S. Pat. Nos. 4,386,179 and 4,613,640, the disclosures of which are incorporated herein by reference. Briefly, the base component of the C-Flex™ material is a Styrene-Ethylene/Butylene-Styrene block copolymer (SEBS). Other components, such as silicone oil, mineral oils, and polypropylene can be added in varying ratios to obtain a desired durometer. "Durometer," as used herein, refers to the hardness of a polymer measured using the Shore A, one second scale for plastics or ASTM Method 2240. From a practical standpoint, the durometer of the shaft and flanged end portion of the ventilation tube can vary within the range of about 20 to about 100, so long as a durometer differential is maintained whereby the shaft material is of higher durometer than the flange material. Shaft 12 is preferably formed of a C-Flex™ polymer or similar material having a durometer of about 90 to about 95. End portion 14 is preferably formed of a C-Flex™ polymer or similar material having a durometer of about 45 to about 55. Examples of other polymeric materials that can be used include Teflon, Silicone and PTFE. An advantage of forming the shaft and-flanged end portion of similar materials, such as the C-Flex™ polymers, is that they can be readily fused or bonded together to form a secure attachment that will not separate during normal implantation and removal procedures.

The ventilation tube 10 described thus far resembles in size and shape a conventional ventilation tube of the type sometimes referred to as a "Goode T-Tube." It will be appreciated, however, that the shaft and flanged end portion of the present invention can be configured in numerous other ways to resemble any type of ventilation and drain tube having a tubular shaft and a flange at one or both ends of the shaft. For example, the ventilation tube of the present invention could resemble in size and shape Touma T-Type, Donaldson, Armstrong, Pope, Collar Button, Per-Lee or Baldwin Butterfly type ventilation tubes.

Figure 5:
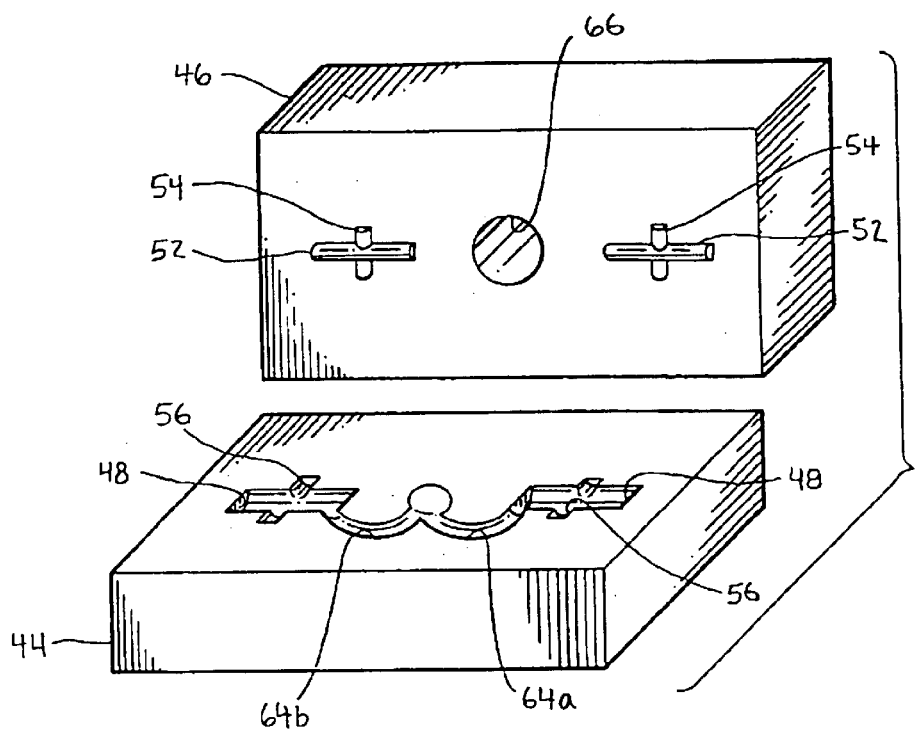
FIG. 5 is an exploded perspective view of a mold used in fabricating a ventilation tube according to the present invention.
Figure 6:
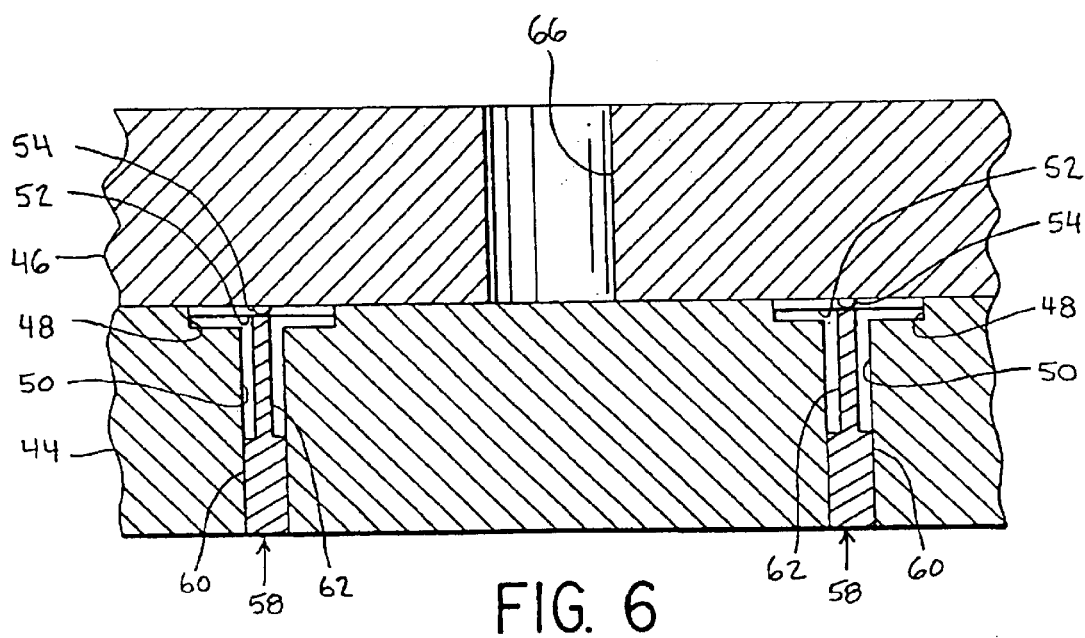
FIGS. 6–10 are fragmentary sectional side views illustrating a method of making a ventilation tube according to the present invention.

The shaft 12 and end portion 14 of the ventilation tube 10 can be fabricated using any suitable manufacturing process and can be secured to one another by thermal or adhesive bonding or by mechanical attachment. A preferred manner of forming the medical ventilation tube 10 is by molding the flanged end portion 14 with the shaft 12 positioned in the mold such that the flanged end portion is formed simultaneously with attachment of the shaft. As shown in FIGS. 5 and 6, the mold has two parts 44 and 46. Mold part 44 has two semicylindrical recesses 48 formed therein in the shape of flanged end part 14; however, any number of recesses can be formed in mold part 44 depending upon the number of medical vent tubes to be made. A through hole 50 extends perpendicularly downward from the bottom of each recess 48 to a bottom face of the mold part to define an outer surface of shaft 12.

Mold part 46 has two semicylindrical projections 52 formed thereon in opposed relation to recesses 48. Projections 52 have a length corresponding to the length of recesses 48 but are of smaller radius to be radially spaced from inside surfaces of recesses 48 when the mold parts are assembled as shown in FIG. 6. The space between projections 52 and recesses 48 correspond in size and shape to flange 26 with the exception of cutouts 34 and 36 which are formed by a second pair of semicylindrical projections 54 that extend transversely across the center of each projection 52 in opposed relation to a pair of similarly sized semicylindrical recesses 56 formed in mold part 44 across recesses 48.

The inner diameter or lumen 22 of each shaft 12 is defined by a core pin 58 disposed within hole 50. Core pin 58 includes a cylindrical base 60 snugly fitted within hole 50 and a post 62 of smaller diameter than the base disposed concentrically within hole 50 between base 60 and projection 52. Channels 64a and 64b connect recesses 48 with a central opening 66 formed through mold part 46 to accommodate a nozzle or the like through which a polymeric material can be injected under pressure.

In forming the medical ventilation tube 10, mold parts 44 and 46 are assembled as shown in FIG. 6 and held together by use of clamps, threaded bolts or any other conventional means to prevent separation of the mold parts when polymeric material is injected into the mold under pressure. In the assembled condition, the projections on mold part 46 fit within the recesses in mold part 44 to define cavities having the shape of flanged end portion 14, and core pins 58 fit within holes 50 to define cavities having the shape of shaft 12.

Figure 7:
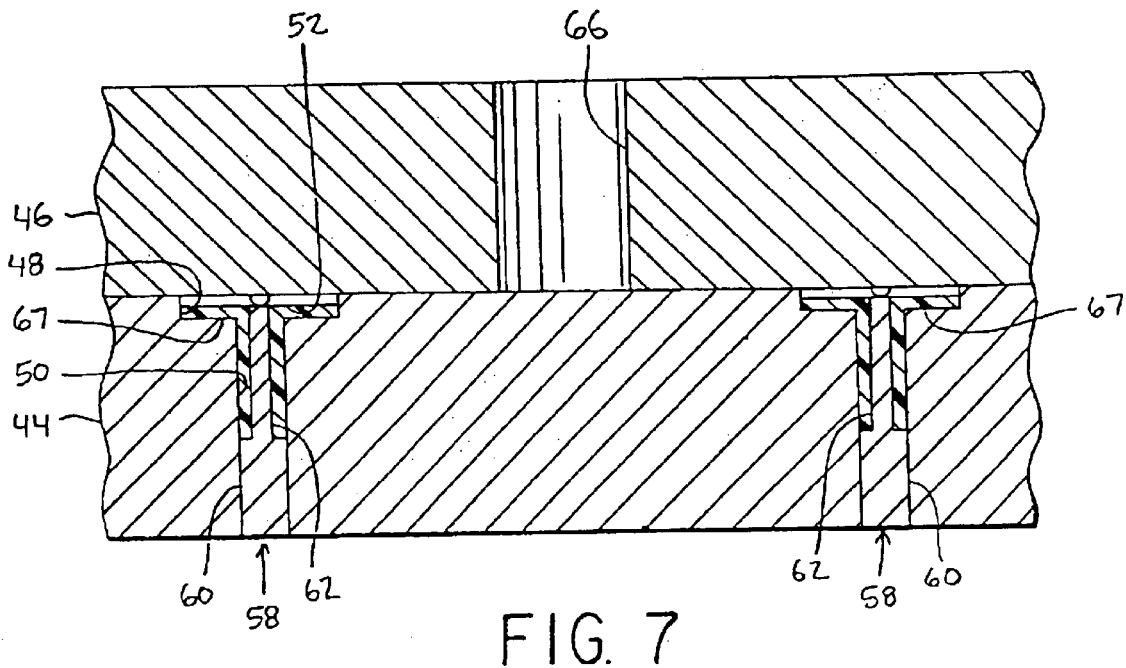

Referring now to FIG. 7, a first polymeric material 67 of relatively high durometer, such as a 90 to 95 durometer C-Flex™ material, is injected into the mold and cured in accordance with the material manufacturer's recommendations to produce a molded part of relatively high durometer resembling the medical ventilation tube. The material is injected into the mold through opening 66 in mold part 46 and is directed by channels 64a and 64b into the space between projections 52 and recesses 48 to form a flanged end portion and between core pin 58 and hole 50 to form the shaft.

Figure 8:
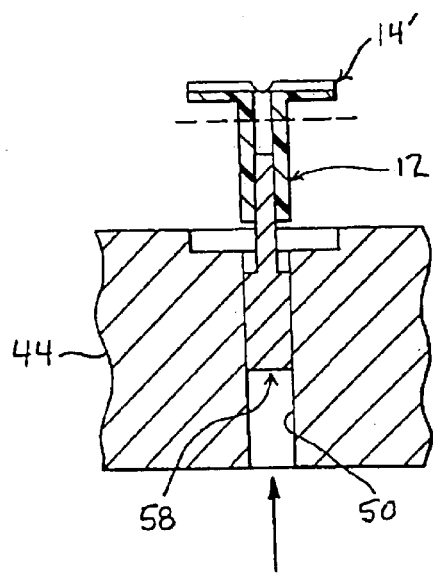
Figure 9:
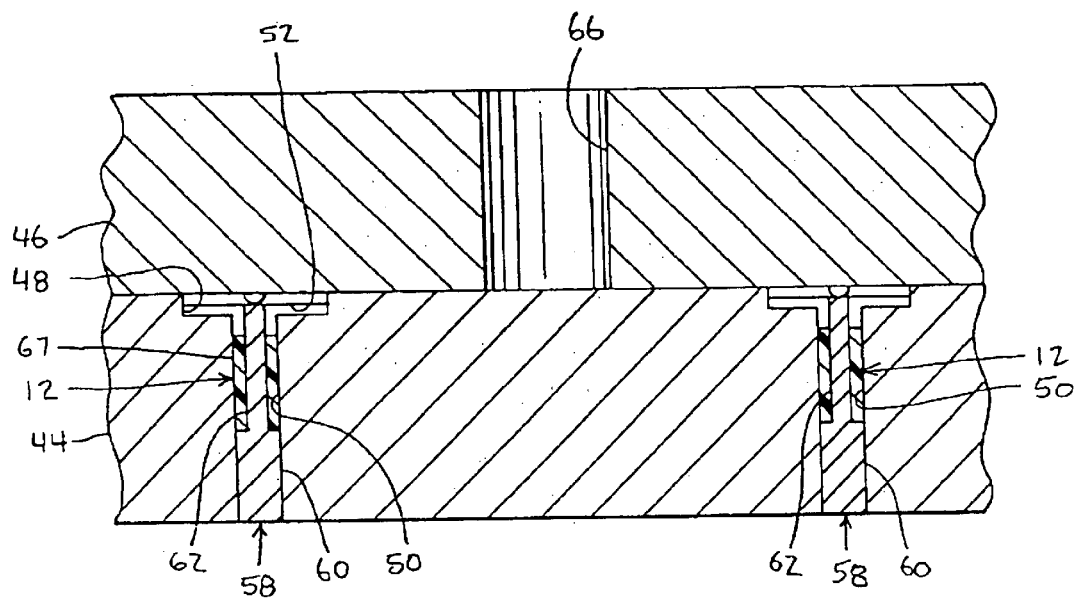
Figure 10:
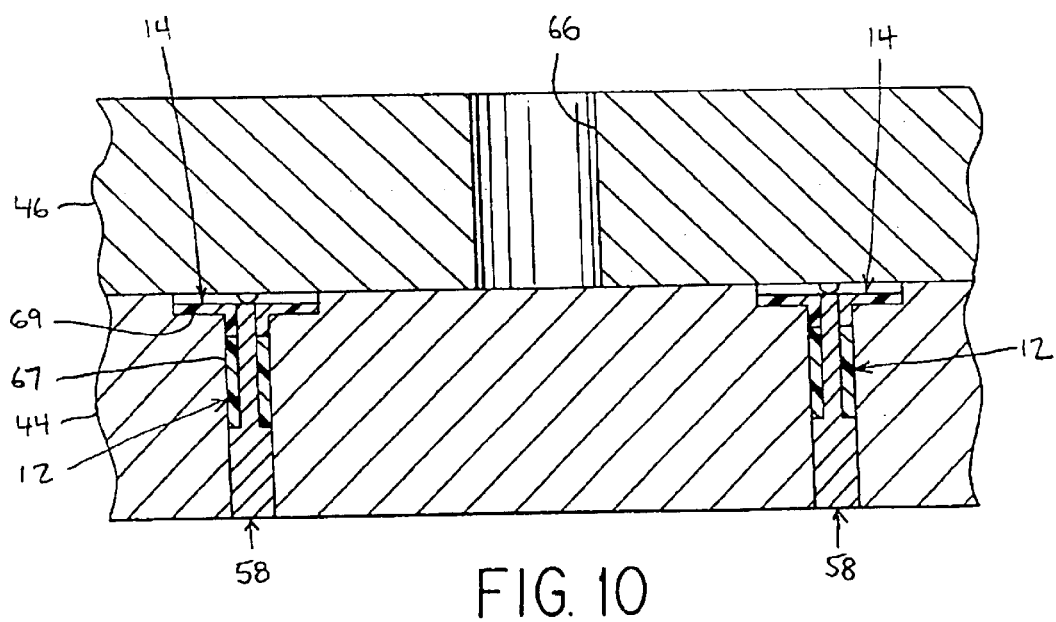

Once the high durometer material has cured, mold parts 44 and 46 are pulled apart and core pins 58 are punched through mold part 44 as shown in FIG. 8 to eject the molded parts. End portion 14' of each molded part is separated from the shaft, for example by cutting across the broken line shown in FIG. 8, and the separated end portion 14' is discarded. Shaft 12 of the molded part is retained so that it can be placed over core pin 58 and positioned within the mold as shown in FIG. 9 when flanged end portion 14 of the medical ventilation tubes is to be formed. Since shaft 12 essentially fills the space between core pin 58 and hole 50, when a second polymeric material 69 of lower durometer than the first, such as a 45 to 55 durometer C-Flex™ material, is injected into the mold, only the cavity having the shape of the flanged end portion will be filled with the low durometer material. As a consequence of molding the flanged ends portion 14 with the shaft 12 positioned in the mold, the flanged end portion will thermally bond with the shaft to form the medical ventilation tube 10 as shown in FIG. 10. When the low durometer material has cured, mold parts 44 and 46 are pulled apart and core pins 58 are punched through the mold part 44 as described previously to eject the medical ventilation tube 10 from the mold.

The manufacturing process described above is exemplary of the types of processes that can be used in forming the medical ventilation tube 10; however, the shaft 12 and end portion 14 of the ventilation tube 10 can be fabricated using any suitable manufacturing process and can be secured to one another using any suitable means of attachment. For example, shaft 12 could be formed using other well known manufacturing methods, such as by extruding a continuous length of hollow tubing and cutting the hollow tubing to a predetermined length corresponding to the length of the shaft. Also, shaft 12 could be made of a metal material, such as stainless steel, and provided with undercuts, grooves or other structural features to facilitate mechanical attachment and retention of the molded end portion 14.

Figure 11:
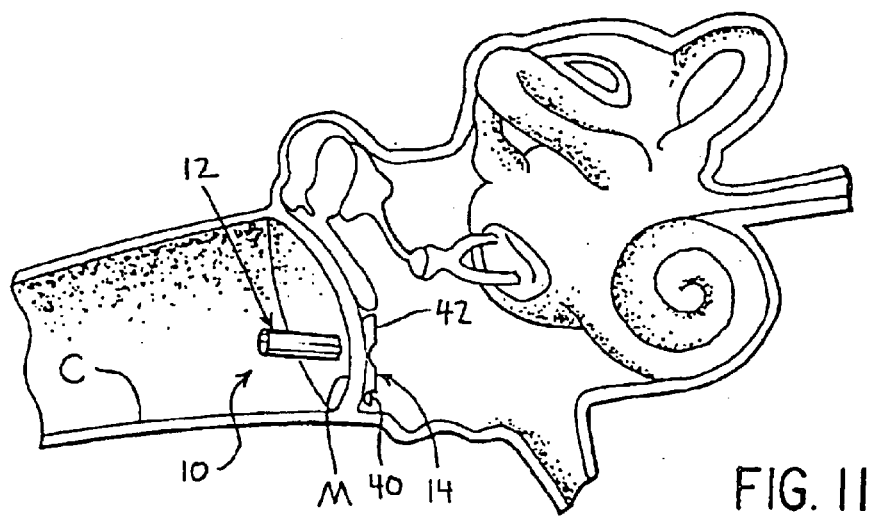
FIG. 11 is a perspective view, partly in section, illustrating use of a ventilation tube according to the present invention.

In use, the ventilation tube 10 can be placed in a myringotomy opening formed in the tympanic membrane of the ear as illustrated in FIG. 11, to treat persistent middle ear effusion or severe otitis media. The ventilation tube 10 is preferably picked up by means of a conventional forceps grasping the proximal end of shaft 12 and is advanced into the auditory canal C of the outer ear toward the tympanic membrane M. Because shaft 12 is formed of a rigid material having a relatively high durometer or hardness, the shaft will resist buckling or bending caused by axial insertion forces, such as those caused by contact with anatomical structures of the ear. As a result, the relatively soft and flexible end portion 14 can be precisely positioned adjacent the myringotomy opening by manipulation of shaft 12 and, when the longitudinal axis of the ventilation tube is substantially aligned with the opening, the end portion of the ventilation tube can be inserted through the opening. When opposed ends, 40 and 42 of the flange pass completely through the opening to be disposed on the opposite, middle ear side of the tympanic membrane, the flange is released and will recover its original transverse shape to prevent accidental extraction or extrusion of the ventilation tube from the opening. The ventilation tube is thus implanted in the tympanic membrane of the ear with shaft 12 placed in the myringotomy opening to maintain a passage of substantially constant diameter through the membrane to allow unobstructed drainage and ventilation of the middle ear over brief or extended periods of time. The ventilation tube can be removed by simply grasping the proximal end of shaft 12 with a forceps and extracting the end portion 14 through the myringotomy opening. As end portion 14 is withdrawn proximally through the opening, the convex side of flange 26 abuts the tympanic membrane such that opposed ends 40 and 42 of the flange are pivoted or forced together in response to the force from tissue contact. Since opposed ends of the flange are semi-cylindrical in cross-section, they cooperate to form a substantially cylindrical profile when pivoted forward thereby easing withdrawal of the ventilation tube from the tympanic membrane without enlarging the myringotomy opening.

Figure 12:
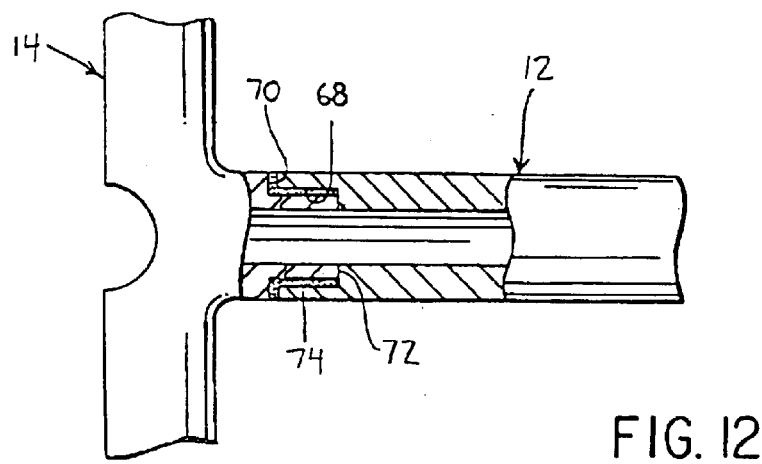
FIG. 12 is a fragmentary side view, partly in section, showing a modification of the ventilation tube according to the present invention.

The shaft and flanged end portion of the ventilation tube can be connected in various ways without compromising strength or performance. For example, in FIG. 12, an alternate connection is shown wherein the distal end of shaft 12 includes a recess 68 and the cylindrical section of end portion 14 includes a shoulder or step 70 joining the cylindrical section with a reduced diameter portion 72 configured to fit within recess 68. Shaft 12 can be made of a high durometer plastic or rigid metal material and is held in place by use of an appropriate adhesive 74 applied to shoulder 70 and/or other parts of the flanged end portion. In forming the alternate connection shown in FIG. 12, flanged end portion 14 is preferably stiffened by mounting on a cylindrical mandrel. After adhesive 74 is applied, shaft 12 can be pushed onto the stiffened end portion and left in place until the adhesive has cured.

Figure 13:
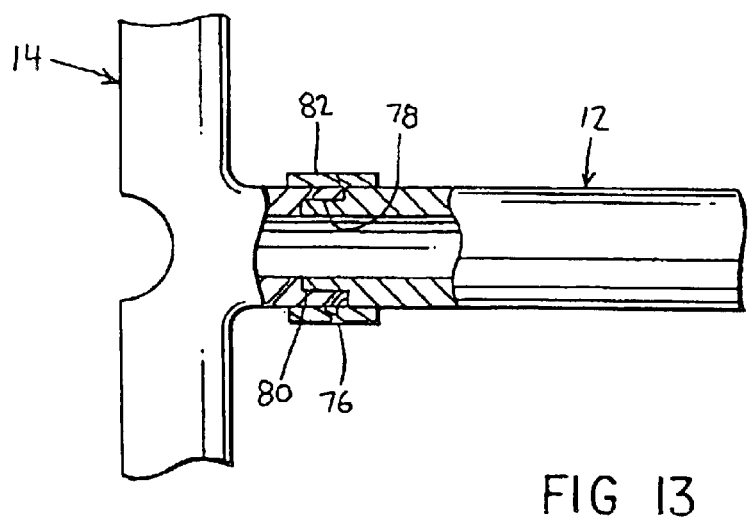
FIG. 13 is a fragmentary side view, partly in section, showing another modification of the ventilation tube according to the present invention.

Another modified connection, shown in FIG. 13, involves forming a step or shoulder 76 at the distal end of shaft 12 and a recess 78 at the proximal end of flanged end portion 14. A reduced diameter portion 80 of shaft 12 extending from shoulder 76 is configured to fit within recess 78 at the proximal end of flanged end portion 14 to serve as a mandrel stiffening the cylindrical section of the flanged end portion. As a result, the shaft and flanged end portion can be held in place with heat shrink tubing 82 or the like that surrounds the end portion in the vicinity of reduced diameter portion 80 of the shaft thereby compressing the end portion against the shaft and producing a tight frictional engagement or bond. Tubing 82 is preferably made of a biocompatible material of relatively thin wall thickness, such as a 0.001–0.002 inch thick Teflon tubing. Pull strength or, in other words, the force required to separate the shaft from the flanged end portion, can be increased by texturing the external surface of reduced diameter portion 80, for example by forming grooves or a cross hatch pattern on the surface or by sand blasting the surface prior to assembly.

From the above, it will be appreciated that, by use of a rigid or hard tubular shaft, the ventilation tube of the present invention can be precisely positioned within an opening formed in an anatomical structure of the body to maintain a passage through the structure over brief or extended periods of time so as to allow unobstructed drainage and ventilation through the anatomical structure. Further, by use of a relatively softer flanged end portion, the ventilation tube of the present invention can prevent accidental extrusion and allow removal without causing significant trauma to the anatomical structure or enlargement of the opening. The ventilation tube can be placed in any anatomical structure separating two regions in need of pressure equalization, such as the tympanic membrane that separates the middle and outer ears. The ventilation tube can have any configuration to fit through an opening in an anatomical structure while preventing inadvertent extrusion, including configurations utilizing T-Type or round flanges and grommet configurations wherein flanges are arranged in spaced relation along the length of the tubular shaft. By "tubular" is meant having a passage extending between open ends; and, while the ventilation tube of the present invention is described herein as having a tubular shaft of cylindrical configuration, it will be appreciated that tubular shafts of any cross-sectional configuration can be used, including elliptical and polygonal cross-sectional configurations. Further, the tubular shaft can be straight, curved or angled depending upon procedural, use; and, when one or more flanges are to be mounted on the shaft, the flanges can be oriented at any angle relative to a longitudinal axis of the shaft.

The material specifications and dimensions of the ventilation tube will vary according to the intended use and, as such, it will be appreciated that the particular materials and dimensions listed herein are merely exemplary and not meant to be limiting.

Inasmuch as the present invention is subject to many variations, modifications and changes in detail, it is intended that all subject matter discussed above or shown in the accompanying drawings be interpreted as illustrative only and not, be taken in a limiting sense.

What is claimed is:

1. A medical ventilation tube for placement in an anatomical structure comprising a hollow tubular shaft having a distal end for placement in the anatomical structure and a passage formed therethrough, said hollow tubular shaft being made of a first material having a rigidity to resist bending and maintain said passage in an open condition when said distal end is placed in the anatomical structure; and a flange extending outwardly from said distal end of said hollow tubular shaft, said flange being made of a second material having a rigidity sufficiently less than that of said first material to permit said flange to deform in response to contact with the anatomical structure during placement of said distal end in and removal of said distal end from the anatomical structure.

2. A medical ventilation tube as recited in claim 1 and further comprising a cylindrical section secured to said distal end of said hollow tubular shaft, said cylindrical section and flange being of integral one-piece construction.

3. A medical ventilation tube as recited in claim 2 wherein said cylindrical section and said hollow tubular shaft have substantially the same outer circumference.

4. A medical ventilation tube as recited in claim 3 wherein said cylindrical section and said hollow tubular shaft abut one another, and wherein abutting portions of said cylindrical section and said hollow tubular shaft are bonded together.

5. A medical ventilation tube as recited in claim 1 wherein said first material is a metal and said second material is a polymer.

* * * * *